United States Patent
Palkrishnan et al.

(10) Patent No.: US 6,335,001 B1
(45) Date of Patent: *Jan. 1, 2002

(54) CARRIER BLENDS FOR DENTIFRICES COMPRISING ETHOXLATED POLYHYDRIC ALCOHOLS

(75) Inventors: Sridhar Palkrishnan, Grosse Ile; Kathleen M. Guiney, Wyandotte, both of MI (US)

(73) Assignee: BASF Corporation, Mount Olive, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/472,488

(22) Filed: Dec. 27, 1999

(51) Int. Cl.$^7$ .................................................. A61K 7/16
(52) U.S. Cl. .......................................................... 424/49
(58) Field of Search ................................... ; A61K 7/16

(56) References Cited

U.S. PATENT DOCUMENTS

| | | |
|---|---|---|
| 2,798,053 A | 7/1957 | Brown |
| 2,923,692 A | 2/1960 | Ackerman et al. |
| 2,980,655 A | 4/1961 | Glass et al. |
| 4,276,430 A | 6/1981 | Reller et al. |
| 4,478,853 A | 10/1984 | Chaussee |
| 4,623,537 A * | 11/1986 | Kearns .................. 424/49 |
| 4,687,663 A | 8/1987 | Schaeffer |
| 4,745,231 A | 5/1988 | Lange et al. |
| 5,059,417 A | 10/1991 | Williams et al. |
| 5,135,748 A * | 8/1992 | Ziegler et al. ............. 424/401 |
| 5,169,624 A * | 12/1992 | Ziegler et al. ................ 424/89 |
| 5,279,816 A | 1/1994 | Church et al. |
| 5,292,527 A | 3/1994 | Konopa |
| 5,380,528 A * | 1/1995 | Alban et al. ............... 424/401 |
| 5,407,668 A | 4/1995 | Kellner |
| 5,420,118 A * | 5/1995 | Alban et al. ................. 514/63 |
| 5,424,070 A | 6/1995 | Kasat et al. |
| 5,665,366 A | 9/1997 | Rawlings et al. |
| 5,690,911 A | 11/1997 | Mirajkar et al. |
| 5,707,635 A * | 1/1998 | Deckner et al. ............. 424/401 |
| 5,709,852 A * | 1/1998 | Gopalkrishnan et al. . 424/78.08 |
| 5,855,874 A * | 1/1999 | Gopalkrishnan et al. ...... 424/52 |
| 5,858,340 A * | 1/1999 | Briggs et al. ............. 424/70.19 |
| 5,863,521 A * | 1/1999 | Schaefer et al. .............. 424/52 |
| 5,866,527 A * | 2/1999 | Mertens ...................... 510/422 |
| 5,908,612 A * | 6/1999 | Dailey et al. ................. 424/49 |
| 5,911,915 A * | 6/1999 | Fonsny et al. .............. 252/312 |
| 5,919,830 A * | 7/1999 | Gopalkrishnan et al. . 514/772.1 |
| 6,037,328 A * | 3/2000 | Hu et al. ....................... 514/23 |
| 6,080,706 A * | 6/2000 | Blanvalet et al. ........... 516/108 |

\* cited by examiner

*Primary Examiner*—Shep K. Rose
(74) *Attorney, Agent, or Firm*—David T. Banchik

(57) ABSTRACT

There is provided a stable non-aqueous carrier for personal care compositions comprising:
  a) 80–98% by weight of a liquid polyoxyalkylene compound comprising a reaction product of an alcohol having 3 to 6 hydroxyl groups and ethylene oxide; and
  b) 2–20% by weight of a solid nonionic polyoxyalkylene compound selected from the group consisting of:
    i) solid nonionic triblock surfactants comprising an inner polyoxypropylene block and two outer polyoxyethylene blocks, wherein the number average molecular weight of the polyoxypropylene block is from about 2000 to about 2900, and the polyoxyethylene content is about 70 to 80 weight percent, based on the total molecular weight of the triblock surfactant;
    ii) solid polyethylene oxide having a number average molecular weight of greater than about 2000; and
    iii) mixtures thereof.

There are also provided dentifrice compositions comprising the stable non-aqueous carrier.

23 Claims, No Drawings

CARRIER BLENDS FOR DENTIFRICES COMPRISING ETHOXLATED POLYHYDRIC ALCOHOLS

FIELD OF THE INVENTION

The present invention relates to stable non-aqueous non-ionic copolymer blends useful as carriers for personal care products.

BACKGROUND OF THE INVENTION

Non aqueous personal care compositions typically contain major amounts of a non-aqueous carrier which provides a suitable matrix into which the active ingredients, and other functional ingredients are added to form a personal care product that is easy to use. It is known in the art that the non-aqueous carrier can be composed of a blend of liquid component(s) and solid component(s) to provide a stable suspension during the formulation of said personal care compositions. For example, the liquid components in a toothpaste formula can be polyethylene glycol of low molecular weight, typically in the range of 200–400. Other liquid components, such as glycerol, or polypropylene glycol can also be used. The solid component, which is usually added to modify the rheology of the composition, can be a higher molecular weight polyethylene glycol of molecular weights between 1,000–10,000. The solid component can also be a nonionic surfactant, such as a triblock copolymer of ethylene oxide/propylene oxide/ethylene oxide (EO/PO/EO). Said solid nonionic surfactant typically consists of 80% ethylene oxide and has a molecular weight usually greater than about 10,000.

In addition to compatibility with the active ingredients and other functional ingredients commonly found in personal care compositions, it is required that the non-aqueous carriers be stable. That is, the compositions should show no phase separation and maintain adequate viscosity when subjected to a variety of conditions, including extreme temperatures, changes of temperature, and shear conditions. Stability of the non-aqueous carriers and the personal care compositions made from them thus can translate to the ease of manufacture of the compositions and to the stability of the compositions when in use by the consumer.

Further, personal care products, such as toothpastes, mouthwashes, cosmetic creams, gels and lotions, antiperspirants, deodorants, and over-the-counter medicaments such as salves and ointments, are subject to freeze-thaw cycles during shipment and storage. Subjecting personal care products to several freeze thaw cycles can alter the an rheology of the product, creating a product dispensing problem when the product becomes too hard or too soft or too viscous, and hence, difficult to use. Thus, non-aqueous carrier compositions and the personal care compositions made from them should be stable to freeze-thaw conditions.

Although other compositions comprising liquid and solid nonionic components are known, which are stable under the above conditions, it is unknown in the art to combine a liquid polyoxyethylene compound comprising an ethoxylated polyhydric alcohol with a solid nonionic polyoxyalkylene compound such as described below.

SUMMARY OF THE INVENTION

There is provided a stable non-aqueous carrier for personal care compositions comprising:
 a) 80–98% by weight of a liquid polyoxyalkylene compound comprising a reaction product of an alcohol having 3 to 6 hydroxyl groups and ethylene oxide; and
 b) 2–20% by weight of a solid nonionic polyoxyalkylene compound selected from the group consisting of:
  i) solid nonionic triblock surfactants comprising an inner polyoxypropylene block and two outer polyoxyethylene blocks, wherein the number average molecular weight of the polyoxypropylene block is from about 2000 to about 2900, and the polyoxyethylene content is about 70 to 80 weight percent, based on the total molecular weight of the triblock surfactant;
  ii) solid polyethylene oxide having a number average molecular weight of greater than about 2000; and
  iii) mixtures thereof.

There are also provided dentifrice compositions comprising the stable non-aqueous carrier.

DETAILED DESCRIPTION OF A PREFERRED EMBODIMENT

Liquid polyoxyalkylene compounds of the present invention can be prepared by means well known in the art by reacting a polyhydric alcohol with appropriate amounts of ethylene oxide in the presence of an alkaline catalyst. The resulting polyether, which may also be called an ethoxylated polyhydric alcohol, may be optionally neutralized with neutralization acids well known in the art. See, for example, *Block & Graft Copolymerization*, Volume 2, Chapter 1, edited by R. J. Ceresa (Wiley, 1981), hereby incorporated by reference.

Polyhydric alcohols useful for making the liquid polyoxyalkylene compounds of the present invention are generally those that have from 3 to 6 hydroxyl groups. Examples of polyhydric alcohols include, but are not limited to, glycerol, trimethylolpropane, 1,2,6-hexanetriol, ditrimethylolpropane, pentaerythritol, glucose, and sorbitol. The liquid polyoxyalkylene compound thus comprises a reaction product of an alcohol having 3 to 6 hydroxyl groups and an appropriate amount of ethylene oxide.

The ethoxylated polyhydric alcohols are characterized by a degree of ethoxylation such that they are liquids, particularly at room temperature or at about 20°–25° C. It is preferable that they be liquid over a wider range of temperature so that flexibility can be gained during their preparation, handling, storage and use by the consumer. It is most preferred that the ethoxylated polyhydric alcohols be liquid down to a temperature of about 0° C. and up to a temperature of about 60° C. Generally, if the ethoxylated polyhydric alcohol is a liquid at room temperature, there will be no problem with it continuing to be a liquid at higher temperatures, i.e., at 60° C. and above. As the temperature is lowered, the ethoxylated polyhydric alcohols of the invention generally will become more viscous until a temperature is reached below which the ethoxylated polyhydric alcohol will no longer pour. The requirement of being liquid at a certain temperature is met if the pour point of the composition is below that temperature. Thus, the liquid polyoxyalkylene compounds of the present invention comprising ethoxylated polyhydric alcohols will generally exhibit good pour properties over the temperature range of about 0° C. up to 60° C. and above.

An example of an ethoxylated polyhydric alcohol is ethoxylated glycerol. In general, the level of ethoxylation should be such that the ethoxylated glycerol is a liquid. If desired, minor amounts of propylene oxide may be incorporated into the ethoxylated glycerol to make an otherwise solid ethoxylate liquid. The ethoxylated glycerol may also be made with only ethylene oxide. It is preferred that the level of ethoxylation on the ethoxylated glycerol not exceed about 60 units of ethylene oxide per glycerol molecule. Preferably, the level of ethoxylation on the ethoxylated glycerol will be less than about 20 units of ethylene oxide per glycerol molecule, typically from about 5 to about 20 units of ethylene oxide per glycerol molecule. A particularly preferred ethoxylated glycerol has a level of ethoxylation of about 12 units of ethylene oxide per glycerol molecule. Another preferred ethoxylated glycerol has a level of ethoxylation of about 10 units of ethylene oxide per glycerol molecule.

The carrier compositions generally comprise from about 80% to about 98% by weight of the liquid polyoxyalkylene compounds described above, preferably from about 85% to about 95%, and most preferably from about 88% to about 92% by weight.

The stable non-aqueous carriers of the present invention also comprise a solid nonionic polyoxyalkylene compound. This nonionic polyoxyalkylene compound can be either a solid nonionic triblock surfactant, a solid polyethylene oxide compound, or mixtures thereof.

Solid nonionic triblock surfactants include those having an inner polyoxypropylene block and two outer polyoxyethylene blocks. Preferred solid nonionic triblock surfactants have a polyoxypropylene block with a number average molecular weight of from about 2000 to about 2900. Furthermore, preferred triblock surfactants have a polyoxyethylene content of about 70–80%, based on the total molecular weight of the triblock surfactant.

Preferred triblock surfactants, having a polyoxypropylene block with a number average molecular weight of about 2000 to about 2900 and a polyoxyethylene content of about 70 to about 80 percent based on the total molecular weight of the triblock surfactant, include PLURONIC® F-98 and PLURONIC® F-88, commercially available from BASF Corporation.

Solid polyethylene oxides are also useful as the solid nonionic polyoxyalkylene compounds of the present invention. These include polyethylene oxides or polyethylene glycols having a number average molecular weight of above about 2000. Preferred polyethylene oxides are those having a number average molecular weight greater than or equal to about 4000. Examples include PEG 4000, PEG 4500, and PEG 6000. Such solid polyethylene oxide compounds are commercially available from a variety of sources. Examples include PLURACOL® E-4000 AND PLURACOL® E-6000, both available from BASF Corporation.

The solid nonionic polyoxyalkylene compound is generally present at a level of from about 2% to about 20% by weight, based on the total weight of the non-aqueous carrier composition. Preferably, it will be present at a level of about 5% to about 15% and most preferably at a level of about 8% to about 12% by weight.

The stable, non-aqueous carrier blends useful in personal care compositions are prepared by blending the liquid polyoxyalkylene compound with the solid nonionic polyoxyalkylene compound. Preferably, 80–98% by weight of the liquid polyoxyalkylene compound is blended with 2–20% by weight of the solid nonionic polyoxyalkylene compound. More preferably, 85–95% by weight of the liquid polyoxyalkylene compound is blended with 5–15% by weight of the solid nonionic polyoxyalkylene compound. Most preferably, 88–92% of the liquid polyoxyalkylene compound is blended with 8–12% of the solid nonionic polyoxyalkylene compound.

The resulting composition is then heated to about 70° C. or until a clear, single-phase composition is obtained. The composition is then cooled with stirring on a Lightnin® mixer set at 100 rpm until the temperature of the composition is ambient (about 35° C.). The composition is then allowed to equilibrate for 24 hours at room temperature (about 25° C.). At the end of the equilibration period, the composition is opaque in appearance and has the consistency of a ointment paste. The viscosity of the composition can then be determined using a Brookfield Cone/Plate rotational viscometer.

As shown in Table 1, the liquid polyoxyalkylene compounds of the invention are good solvents for flavoring oils, whereas glycerol, commonly used as a component of non-aqueous carrier compositions, is not. In Table 1, 0.2% solutions of the flavoring oils in the ethoxylated polyhydric alcohols (exemplified by a glycerol 12 mole ethoxylate) gave clear solutions while the solutions in glycerol were hazy.

This property leads to advantages in formulating dentifrice compositions of the invention. For example, a flavor oil may be added to the nonaqueous carrier blend of the invention to accomplish good incorporation of the flavor oil into the dentifrice composition. Suitable flavoring oils include but are not limited to oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. A flavor system is generally used in the compositions at levels of from about 0.001 percent to about 5 percent by weight of the composition.

TABLE 1

Solutions of 0.2% flavor oils in ethoxylated polyhydric alcohol

| PRODUCT | EUCALYPTUS OIL | CAMPHOR | METHYL SALICYLATE | MENTHOL | THYMOL |
| --- | --- | --- | --- | --- | --- |
| GLYCEROL | Hazy | Hazy | Hazy | Hazy | Hazy |
| GLYCEROL + 12 eo | Clear | Clear | Clear | Clear | Clear |

Table 2 presents a comparison of the physical properties of glycerin and three different ethoxylated polyhydric alcohols (represented by ethoxylated glycerol with levels of ethoxylation from 10 to 20). It is seen that whereas glycerol has a sweet taste, the glycerol ethoxylates are essentially tasteless. That is, the ethoxylated polyhydric alcohols of the present invention do not have the sweet taste of glycerin. This may provide a benefit to formulators who do not prefer the sweet taste of glycerin. Formulators using glycerin in such compositions often have to rely upon expensive flavoring agents to mask the sweet taste imparted by glycerin. Since glycerol ethoxylates are essentially tasteless, the use of masking agents in dentifrice compositions can be minimized. Alternatively, sweetening agents can be added to dentifrice compositions of the instant invention to compensate for the lack of sweetness. These include saccharin, dextrose, sucrose, lactose, maltose, levulose, aspartame, sodium cyclamate, D-tryptophan, dihydrochalcones, acesulfame, and mixtures thereof.

TABLE 2

| PRODUCT | TASTE | POUR POINT |
| --- | --- | --- |
| GLYCEROL | SWEET | 17° C. |
| GLYCEROL-10 MOLE EO | TASTELESS | −39° C. |
| GLYCEROL-12 MOLE EO | TASTELESS | not determined. |
| GLYCEROL-20 MOLE EO | TASTELESS | −5° C. |

Preparation of Personal Care Compositions Containing the Stable Non-Aqueous Carrier Blends of the Present Invention Personal care compositions preferably comprise 10–90% by weight of the stable non-aqueous carrier blends of the present invention, more preferably 25–85%, and most preferably, 40–80% by weight.

Personal care formulations comprising these stable non-aqueous carrier blends may further comprise other ingredients such as surfactants selected from anionic surfactants, such as sodium lauryl sulphate, sodium alkyl glyceryl ether sulfonate, and alkylbenzene sulfonates. Further, small amounts of cationic surfactants, having a quaternary nitrogen, which show compatibility with the nonionic carrier blends of this invention can also be used. Various other materials may also be used in the formulating of personal care products. For example, in a dentifrice, dental abrasives consisting of freely divided silica, or calcium carbonate, calcium pyrophosphate, and hydrated alumina are added for polishing performance. Additionally, thickening agents such as xanthan gum, gum arabic, and hydroxyethylcellulose can also be used to provide sufficient thickening consistency to the formulation. Also, flavoring agents such as peppermint, spearmint oils or preservatives, opacifying agents, buffer salts, sweeteners, anti-bacterial agents or anti-plaque agents, anti-inflammatory agents, and anti-caries agents such as the fluoride salts can also be included in small amounts. Polymeric agents which accelerate the transport of active materials can also be included. Also, in cosmetic creams emollients such as glycerin, mineral oil and petrolatum can be added.

Personal care products are formulated according to methods known to those skilled in the art. Representative personal care product formulations are disclosed in: *Cosmetics, Science and Technology,* 2nd Edition, Vol. 1, Edited by M. S. Balsam, et al., and *A Formulary of Cosmetic Preparations,* Michael and Irene Ash, Chemical Publishing, N.Y., N.Y., both incorporated by reference herein.

The following non-limiting Examples serve to illustrate the utility of the present invention. All percentages are weight percent (%) of the total composition unless otherwise indicated.

Dentifrice Composition 10 to 55% abrasive, selected from the group including, but not limited to, anhydrous dicalcium phosphate, calcium carbonate, calcium pyrophosphate.

0.2 to 0.8% stannous fluoride, sodium monofluorophosphate 2 to 10% binders, including, but not limited to, gum karaya, tragacanth USP, sodium alginate; Irish moss and methyl cellulose.

2 to 8% surfactants, including, but not limited to, sodium lauryl sulfate, sodium-N-lauryl sarcosinate; dioctyl sodium sulfosuccinate.

10 to 50% humectants, including, but not limited to, glycerol; propylene glycol; sorbitol; polyethylene glycol.

25 to 85% non-aqueous carrier blend of the present invention comprising:
a) 80–98% by weight of a liquid polyoxyalkylene compound comprising a reaction product of an alcohol having 3 to 6 hydroxyl groups and ethylene oxide; and
b) 2–20% by weight of a solid nonionic polyoxyalkylene compound selected from the group consisting of:
  i) solid nonionic triblock surfactants comprising an inner polyoxypropylene block and two outer polyoxyethylene blocks, wherein the number average molecular weight of the polyoxypropylene block is from about 2000 to about 2900, and the polyoxyethylene content is about 70 to 80 weight percent, based on the total molecular weight of the triblock surfactant;
  ii) solid polyethylene oxide having a number average molecular weight of greater than about 2000; and
  iii) mixtures thereof.

EXAMPLES

The Examples show stability of various blends of an ethoxylated polyhydric alcohol (exemplified by glycerol plus 12 moles EO) with a series of solid nonionic polyoxyalkylene compounds. The blends were prepared by the method described above. Each Example contained 90% by weight of ethoxylated glycerol with an ethoxylation level of about 12, and 10% by weight of the solid polyoxyalkylene compounds listed. Results are given for tests of room temperature stability, high temperature stability, and freeze/thaw stability.

Room temperature stability refers to a test where the compositions are held at 25° C. for a period of two months. After two months, the compositions are visually inspected for phase separation or other changes. A stable composition at the end of the two-month period is reported if the composition is a homogeneous single-phase system. An unstable composition is reported if the composition splits into two phases.

For the freeze/thaw stability test, the compositions of the Examples were put through three cycles of freezing and thawing. After the tests, the samples are visually examined for stability as above in the room temperature stability test.

The third test, for high temperature stability, involves holding the compositions of the Examples in a 50° C. oven for a period of two months. Thereafter, stability was determined as above for the room temperature stability and the freeze/thaw stability tests.

Preferred solid nonionic compounds exhibit stability in the room temperature stability test, the freeze/thaw stability test, and the high temperature stability test. It is noted in Examples 3 and 4 that PLURONIC® F-98 and PLURONIC® F-88 show stability in the three tests.

Examples 7–11 show a series of polyethylene oxides. It is seen in Examples 10 and 11 that the solid ethylene oxides having a molecular weight greater than about 2000 show stability in the high temperature stability test. The polyethylene oxides with molecular weight 2000 or lower, exemplified in Examples 7–9, are unstable in the high temperature stability test.

EXAMPLES 1–11

| Ex. | Molecular Weight | Solid polyoxyalkylene compound | Melting Point | Room Temperature Stability | Freeze/Thaw Stability | High Temp Stability |
|---|---|---|---|---|---|---|
| 1 | 12600 | Pluronic F-127 | 56 | Stable | Stable | Unstable |
| 2 | 14600 | Pluronic F-108 | 57 | Stable | Stable | Unstable |
| 3 | 13000 | Pluronic F-98 | 58 | Stable | Stable | Stable |
| 4 | 11400 | Pluronic F-88 | 54 | Stable | Stable | Stable |
| 5 | 8400 | Pluronic F-68 | 52 | Stable | Stable | Unstable |
| 6 | 4700 | Pluronic F-38 | 48 | Stable | Stable | Unstable |
| 7 | 1000 | PEG 1000 | | Not Determined | Not Determined | Unstable |
| 8 | 1450 | PEG 1450 | | Not Determined | Not Determined | Unstable |
| 9 | 2000 | PEG 2000 | | Not Determined | Not Determined | Unstable |
| 10 | 4000 | PEG 4000 | | Not Determined | Not Determined | Stable |
| 11 | 4500 | PEG 4500 | | Not Determined | Not Determined | Stable |

What is claimed is:

1. A stable non-aqueous carrier for personal care compositions comprising:
   a) 80–98% by weight of a liquid polyoxyalkylene compound comprising a reaction product of an alcohol having 3 to 6 hydroxyl groups and ethylene oxide; and
   b) 2–20% by weight of a solid nonionic polyoxyalkylene compound selected from the group consisting of:
      i) solid nonionic triblock surfactants comprising an inner polyoxypropylene block and two outer polyoxyethylene blocks, wherein the number average molecular weight of the polyoxypropylene block is from about 2000 to about 2900, and the polyoxyethylene content is about 70 to 80 weight percent, based on the total molecular weight of the triblock surfactant;
      ii) solid polyethylene oxide having a number average molecular weight of greater than about 2000; and
      iii) mixtures thereof.

2. A stable non-aqueous carrier according to claim 1, wherein said solid nonionic polyoxyalkylene compound comprises polyethylene oxide having a number average molecular weight greater than or equal to about 4000.

3. A stable non-aqueous carrier according to claim 1, wherein said solid nonionic polyoxyalkylene compound comprises solid nonionic triblock surfactants.

4. A stable non-aqueous carrier according to claim 1, wherein said liquid polyoxyalkylene compound comprises ethoxylated glycerol having a level of ethoxylation of less than about 60.

5. A stable non-aqueous carrier according to claim 1, wherein said liquid polyoxyalkylene compound comprises ethoxylated glycerol having a level of ethoxylation of less than about 20.

6. A stable non-aqueous carrier according to claim 1, wherein said liquid polyoxyalkylene compound comprises ethoxylated glycerol having a level of ethoxylation of about 5 to about 20.

7. A stable non-aqueous carrier according to claim 1, wherein said liquid polyoxyalkylene compound comprises ethoxylated glycerol having a level of ethoxylation of about 12.

8. A stable non-aqueous carrier according to claim 1, wherein said liquid polyoxyalkylene compound comprises ethoxylated glycerol, having a level of ethoxylation of about 10.

9. A stable non-aqueous carrier for personal care compositions comprising:
   a) 80–98% by weight of a liquid polyoxyalkylene compound comprising an ethoxylated glycerol; and
   b) 2–20% by weight of solid nonionic triblock surfactants comprising an inner polyoxypropylene block and two outer polyoxyethylene blocks, wherein the number average molecular weight of the polyoxypropylene block is from about 2000 to about 2900, and the polyoxyethylene content is about 70 to 80 weight percent, based on the total molecular weight of the triblock surfactant.

10. A stable non-aqueous carrier according to claim 9, wherein said liquid polyoxyalkylene compound comprises ethoxylated glycerol having a level of ethoxylation up to about 60.

11. A stable non-aqueous carrier according to claim 9, wherein said liquid polyoxyalkylene compound comprises ethoxylated glycerol having a level of ethoxylation of up to about 20.

12. A stable non-aqueous carrier according to claim 9, wherein said liquid polyoxyalkylene compound comprises ethoxylated glycerol having a level of ethoxylation of about 5 to 20.

13. A stable non-aqueous carrier according to claim 9, wherein said liquid polyoxyalkylene compound comprises ethoxylated glycerol having a level of ethoxylation of about 12.

14. A stable non-aqueous carrier according to claim 9, wherein said liquid polyoxyalkylene compound comprises ethoxylated glycerol having a level of ethoxylation of about 10.

15. A stable non-aqueous carrier for personal care compositions comprising:
   a) 80–98% by weight of a liquid polyoxyalkylene compound comprising an ethoxylated glycerol; and
   b) 2–20% by weight of a solid polyethylene oxide having a number average molecular weight of greater than or equal to about 4000.

16. A stable non-aqueous carrier according to claim 15, wherein said liquid polyoxyalkylene compound comprises ethoxylated glycerol having a level of ethoxylation up to about 60.

17. A stable non-aqueous carrier according to claim 15, wherein said liquid polyoxyalkylene compound comprises ethoxylated glycerol having a level of ethoxylation of up to about 20.

18. A stable non-aqueous carrier according to claim 15, wherein said liquid polyoxyalkylene compound comprises ethoxylated glycerol having a level of ethoxylation of about 5 to 20.

19. A stable non-aqueous carrier according to claim 15, wherein said liquid polyoxyalkylene compound comprises ethoxylated glycerol having a level of ethoxylation of about 12.

20. A stable non-aqueous carrier according to claim 15, wherein said liquid polyoxyalkylene compound comprises ethoxylated glycerol having a level of ethoxylation of about 10.

21. An anhydrous dentifrice composition comprising 25–85% by weight of a stable non-aqueous carrier according to claim 1.

22. An anhydrous dentifrice composition comprising 25–85% by weight of a stable non-aqueous carrier according to claim 9.

23. An anhydrous dentifrice composition comprising 25–85% by weight of a stable non-aqueous carrier according to claim 15.

* * * * *